United States Patent [19]

Blystone et al.

[11] Patent Number: 5,356,546
[45] Date of Patent: Oct. 18, 1994

[54] METAL SALTS USEFUL AS ADDITIVES FOR FUELS AND LUBRICANTS

[75] Inventors: Sheri L. Blystone, Concord Township, Lake County; William K. S. Cleveland, Mentor on the Lake; Paul E. Adams, Willoughby Hills, all of Ohio

[73] Assignee: The Lubrizol Corporation, Wickliffe, Ohio

[21] Appl. No.: 870,506

[22] Filed: Apr. 16, 1992

[51] Int. Cl.$^5$ .................. C10M 105/08; C09K 3/00; C09K 15/32

[52] U.S. Cl. ............................ 252/35; 556/49; 556/131; 556/147; 252/39; 252/41; 252/389.52; 252/389.61; 252/389.62; 252/460.52; 252/460.53; 252/400.61; 252/400.62; 44/358; 44/363

[58] Field of Search ............ 556/49, 131, 147; 252/35, 39, 41, 389.52, 389.61, 389.62, 400.52, 400.53, 400.61, 400.62

[56] References Cited

U.S. PATENT DOCUMENTS

| | | | |
|---|---|---|---|
| 2,197,834 | 4/1940 | Reiff et al. | 87/9 |
| 2,380,305 | 7/1945 | Gleason et al. | 252/57 |
| 2,933,520 | 4/1960 | Bader | 260/473 |
| 3,038,935 | 6/1962 | Gerber et al. | 260/520 |
| 3,133,944 | 5/1964 | Christenson | 260/434 |
| 3,471,537 | 10/1969 | Berke et al. | 260/429 |
| 3,723,489 | 3/1973 | Dexter et al. | 260/429.7 |
| 3,954,808 | 5/1976 | Elliott et al. | 260/343.2 R |
| 3,966,807 | 6/1976 | Elliott et al. | 260/559 D |
| 4,007,282 | 2/1977 | Mauz et al. | 424/308 |
| 4,046,802 | 9/1977 | Elliott et al. | 260/61 G |
| 4,051,049 | 9/1977 | Elliott et al. | 252/51.5 A |
| 4,083,791 | 4/1978 | Elliott et al. | 252/51.5 A |
| 4,263,167 | 4/1981 | Mago | 252/391 |
| 4,611,016 | 9/1986 | Hinsken et al. | 529/99 |
| 4,828,733 | 5/1989 | Farng et al. | 252/42.7 |
| 4,855,073 | 8/1989 | Murakami et al. | 252/39 |

FOREIGN PATENT DOCUMENTS

| | | | |
|---|---|---|---|
| WO8904358 | 5/1989 | PCT Int'l Appl. | |
| 339217 | 8/1959 | Switzerland. | |
| 1134337 | 11/1968 | United Kingdom | C08G 43/00 |
| 1521567 | 8/1978 | United Kingdom | C08K 5/13 |

*Primary Examiner*—Paul J. Killos
*Assistant Examiner*—Porfirio Nazario
*Attorney, Agent, or Firm*—Joseph P. Fischer; Frederick D. Hunter, Sr.; James L. Cordek

[57] ABSTRACT

This invention relates to metal salts of the general formula $$A^{y-}M^{y+} \qquad (I)$$

wherein M represents one or more metal ions, y is the total valence of all M and A represents one or more anion containing groups having a total of about y individual anionic moieties and each anion containing group is a group of the formula

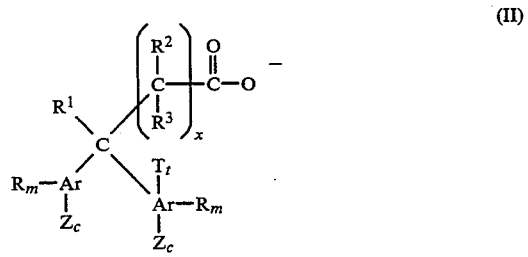

(II)

wherein each group in (II) is as described in the specification. These salts find utility in lubricants and fuels other than 2-cycle engine lubricants and fuels.

75 Claims, No Drawings

METAL SALTS USEFUL AS ADDITIVES FOR FUELS AND LUBRICANTS

FIELD OF THE INVENTION

This invention relates to novel metal salts useful as additives for lubricants based on oils of lubricating viscosity and normally liquid fuels. More particularly, it relates to metal carboxylates of alkylene bis-phenol alkanoic acids.

BACKGROUND OF THE INVENTION

U.S. Pat. No. 2,933,520 to Bader relates to compounds represented by the formula

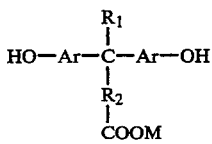

in which $R_1$ may be hydrocarbon, halogen, $R_2$ is hydrocarbon, e.g., alkylene other than methylene and containing at least two carbon atoms and containing up to 10, 12 or even more carbon atoms, Ar groups are aromatic rings, unsubstituted or substituted with alkyl, halogen, nitro, sulfo and others, the nature of each of these groups affecting properties such as boiling point, solubility, toxicity, and bactericidal, fungicidal, insecticidal and like properties.

U.S. Pat. No. 3,038,935 to Gerber et al teaches the preparation of compounds of the formula

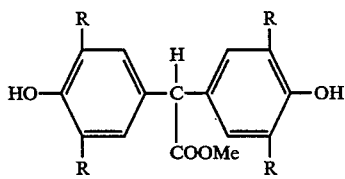

wherein each R is an aliphatic, cycloalipatic or aromatic radical, Me is Na, K or Li, by reacting alkali metal salts of hindered phenols with dichloroacetic acid. Products are said to be useful for production of rubber auxiliaries, mineral oil additives and stabilizers for plastics.

U.S. Pat. No. 3,133,944 to Christensen teaches heavy metal salts represented by

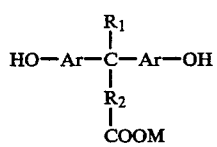

wherein the $R_1$ is alkyl of 1–4 carbons, $R_2$ is alkylene of 2–6 carbons and Ar is an aromatic group which may be substituted with one or more methyl groups and others. The salts are said to be adapted to retard or prevent the growth of biological organisms, particularly molds and mildews.

U.S. Pat. No. 3,471,537 to Berke et al teaches diphenolic compounds of the formulas

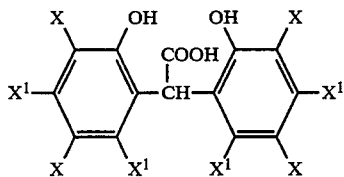

and

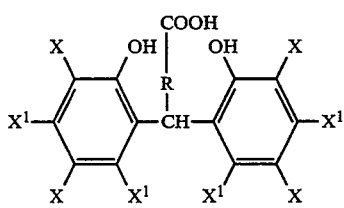

wherein X and $X^1$ are halogen or hydrogen, salts and derivatives as useful for germicides and antiseptics and disinfectants.

U.S. Pat. No. 4,828,733 to Farng et al relates to copper salts of hindered phenol carboxylic acids.

A wide variety of metal-containing compounds have been employed, with varying degrees of success as lubricating oil additives. Illustrative are detergents of the ash-containing type. These are well-known in the art and include Newtonian and non-Newtonian neutral and overbased salts of alkali, alkaline earth and transition metals with, for example, sulfonic acids, carboxylic acids, salicylic acids, phosphorus-containing acids, phenols and the like.

The improvement of the performance characteristics of lubricants based on oils of lubricating viscosity and normally liquid fuels through the use of additives has been known for many years. Still, because of increased raw material and labor costs, increasing fuel and lubricant costs, environmental concerns and more demanding performance requirements arising from higher performance engines and the like, the search for new, effective alternate lubricant and fuel additives continues unabated.

Therefore, it is an object of this invention to provide novel compounds that will act as performance improving additives for oil based lubricants and normally liquid fuels containing such compounds.

It is a further object to provide novel additive concentrates and lubricant and fuel compositions containing the metal salts of this invention.

Other objects will be apparent to those skilled in the art upon review of the present specification.

SUMMARY OF THE INVENTION

This invention relates to metal salts of the general formula $$A^{y-}M^{y+} \qquad (I)$$

wherein M represents one or more metal ions, y is the total valence of all M and A represents one or more anion containing groups having a total of about y individual anionic moieties and each anion containing group is a group of the formula

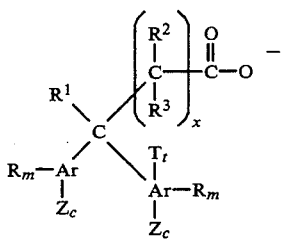

wherein T is selected from the group consisting of

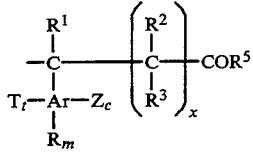

or

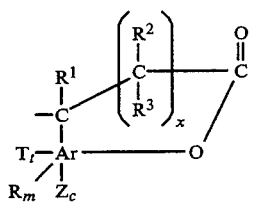

wherein each $R^5$ is independently selected from $O^-$ and $OR^6$ wherein $R^6$ is H or alkyl and each t is independently 0 or 1, wherein T is as hereinbefore defined and wherein each Ar is independently an aromatic group of from 4 to about 30 carbon atoms having from 0 to 3 optional substituents selected from the group consisting of polyalkoxyalkyl, lower alkoxy, nitro, halo or combinations of two or more of said optional substituents, or an analog of such an aromatic group, each R is independently alkyl, alkenyl or aryl containing at least 8 carbon atoms, $R^1$ is H or a hydrocarbyl group, $R^2$ and $R^3$ are each independently H or a hydrocarbyl group, each m is independently an integer ranging from 1 to about 10, x ranges from 0 to about 8, and each Z is independently OH, $(OR^4)_bOH$ or $O^-$ wherein each $R^4$ is independently a divalent hydrocarbyl group and b is a number ranging from 1 to about 30 and c ranges from 0 to about 3 with the proviso that when t in Formula (II)=0, or when T is Formula (V), then c is not 0, provided that the sum of m, c and t does not exceed the unsatisfied valences of the corresponding Ar.

Lubricants based on oils of lubricating viscosity, normally liquid fuels and additive concentrates containing the above-described metal salts are also embodiments of this invention.

DESCRIPTION OF THE PREFERRED EMBODIMENTS

DETAILED DESCRIPTION OF THE INVENTION

The present invention relates to metal salts of the general formula $$A^{y-}M^{y+}$$

wherein M represents one or more metal ions, y is the total valence of all M and A represents one or more anion containing groups having a total of about y individual anionic moieties.

Another way of illustrating the metal salt of this invention is by the formula

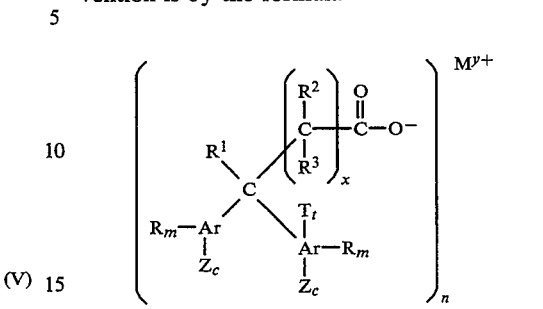

wherein M represents one or more metal ions, y is the total valence of all M, n is a number depending on the value of y, n times the number of anionic moieties in the corresponding parenthetical group is about equal to y, and the remaining elements are as defined hereinabove. Preferably Ar is a benzene nucleus, a bridged benzene nucleus or a naphthalene nucleus.

The Anion-Containing Group A

A represents one or more anion containing groups having a total of about y individual anionic moieties and each anion containing group is a group of the formula

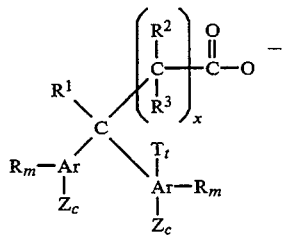

wherein T is selected from the group consisting of

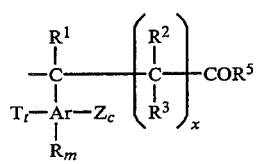

or

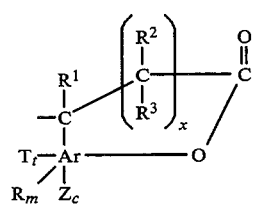

wherein each $R^5$ is independently selected from $O^-$ and $OR^6$ wherein $R^6$ is H or alkyl and each t is independently 0 or 1, wherein T is as hereinbefore defined and wherein each Ar is independently an aromatic group of from 4 to about carbon atoms having from 0 to 3 optional substituents selected from the group consisting of polyalkoxyalkyl, lower alkoxy, nitro, halo or combinations of two or more of said optional substituents, or an analog of such an aromatic nucleus, each R is independently alkyl, alkenyl or aryl containing at least 8 carbon atoms, $R^1$ is H or a hydrocarbyl group, $R^2$ and $R^3$ are each independently H or a hydrocarbyl group, each m is independently an integer ranging from 1 to about 10, x ranges from 0 to about 6, and each Z is independently OH, $(OR^4)_bOH$ or $O^-$ wherein each $R^4$ is independently a divalent hydrocarbyl group and b is a number ranging from 1 to about 30 and c ranges from 0 to about 3 with the proviso that when t in Formula (II)=0, or when T is Formula (V), then c is not 0, provided that the sum of m, c and t does not exceed the unsatisfied valences of the corresponding Ar.

The aromatic group Ar of formula (II) can be a single aromatic nucleus such as a benzene nucleus, a pyridine nucleus, a thiophene nucleus, a 1,2,3,4-tetrahydronaphthalene nucleus, etc., or a polynuclear aromatic moiety. Such polynuclear moieties can be of the fused type; that is, wherein pairs of aromatic nuclei making up the Ar group share two points, such as found in naphthalene, anthracene, the azanaphthalenes, etc. Polynuclear aromatic moieties also can be of the linked type wherein at least two nuclei (either mono or polynuclear) are linked through bridging linkages to each other. Such bridging linkages can be chosen from the group consisting of carbon-to-carbon single bonds between aromatic nuclei, ether linkages, keto linkages, sulfide linkages, polysulfide linkages of 2 to 6 sulfur atoms, sulfinyl linkages, sulfonyl linkages, methylene linkages, alkylene linkages, di-(lower alkyl) methylene linkages, lower alkylene ether linkages, alkylene keto linkages, lower alkylene sulfur linkages, lower alkylene polysulfide linkages of 2 to 6 carbon atoms, amino linkages, polyamino linkages and mixtures of such divalent bridging linkages. In certain instances, more than one bridging linkage can be present in Ar between aromatic nuclei. For example, a fluorene nucleus has two benzene nuclei linked by both a methylene linkage and a covalent bond. Such a nucleus may be considered to have 3 nuclei but only two of them are aromatic. Normally, Ar will contain only carbon atoms in the aromatic nuclei per se.

Specific examples of single ring Ar moieties are the following:

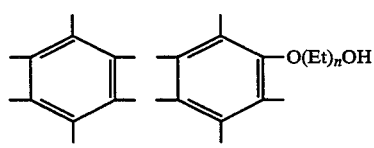

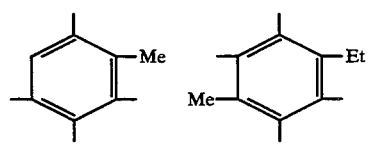

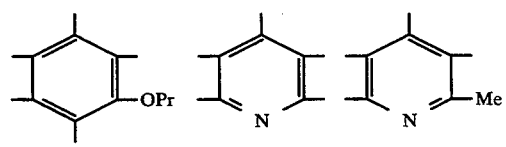

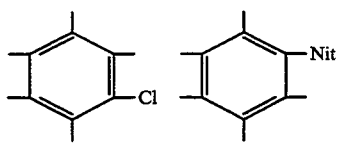

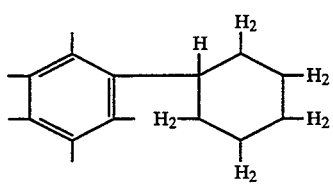

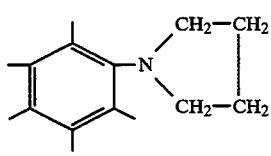

etc., wherein Me is methyl, Et is ethyl or ethylene, as appropriate, Pr is n-propyl, and Nit is nitro.

Specific examples of fused ring aromatic moieties Ar are:

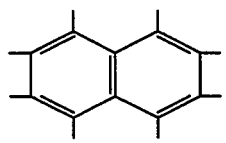

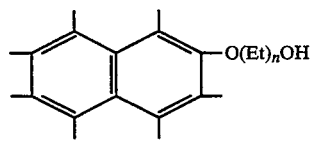

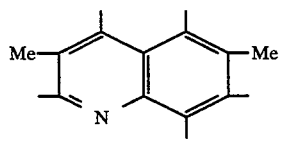

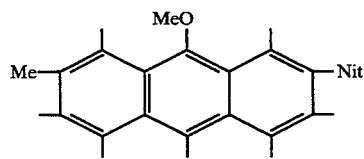

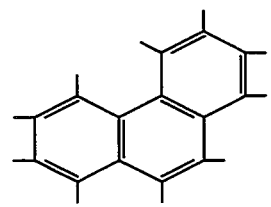

etc.

When the aromatic moiety Ar is a linked polynuclear aromatic moiety, it can be represented by the general formula $$ar\text{-}(L\text{-}ar)_w$$

wherein w is an integer of 1 to about 20, each ar is a single ring or a fused ring aromatic nucleus of 4 to about 12 carbon atoms and each L is independently selected from the group consisting of carbon-to-carbon single bonds between between ar nuclei, ether linkages (e.g. —O—), keto linkages (e.g., $$-\overset{\overset{O}{\|}}{C}-),$$

sulfide linkages (e.g., —S—), polysulfide linkages of 2 to 6 sulfur atoms (e.g., —S—$_{2\text{-}6}$), sulfinyl linkages (e.g., —S(O)—), sulfonyl linkages (e.g., —S(O)$_2$—), lower alkylene linkages (e.g., —CH$_2$—, —CH$_2$—CH$_2$—, —CH—CH—) di(lower alkyl)-methylene linkages
   |
   R°

(e.g., —CR°$_2$—), lower alkylene ether linkages (e.g., —CH$_2$O—, —CH$_2$O—CH$_2$—, —CH$_2$—CH$_2$O—, —CH$_2$CH$_2$OCH$_2$CH—$_2$, —CH$_2$CHOCH$_2$CH—, —CH$_2$CHOCHCH$_2$—, etc.),
   |            |     |
   R°          R°   R° lower alkylene sulfide linkages (e.g., wherein one or more —O—'s in the lower alkylene ether linkages is replaced with a S atom), lower alkylene polysulfide linkages (e.g., wherein one or more —O— is replaced with a —S—$_{2\text{-}6}$ group), amino linkages (e.g.,

—N—, —N—, —CH$_2$N—, —CH$_2$N—,
 |    |         |         |
 H    R°

—CH$_2$NCH$_2$—, —alk—N—,
    |           | where alk is lower alkylene, etc.), polyamino linkages (e.g., —N(alkN)$_{1\text{-}10}$, where the unsatisfied free N valences are taken up with H atoms or R° groups), linkages derived from oxo- or keto- carboxylic acids (e.g.)

wherein each of R$^1$, R$^2$ and R$^3$ is independently hydrocarbyl, preferably alkyl or alkenyl, most preferably lower alkyl, or H, R$^6$ is H or an alkyl group and x is an integer ranging from 0 to about 8, and mixtures of such bridging linkages (each R° being a lower alkyl group).

Specific examples of linked moieties are:

Usually all of these Ar groups have no substituents except for the R and Z groups (and any bridging groups).

For such reasons as cost, availability, performance, etc., Ar is normally a benzene nucleus, a lower alkylene bridged benzene nucleus, or a naphthalene nucleus. Most preferably Ar is a benzene nucleus substituted by an R group in a position para to a Z group.

The Group R

The compounds of formula (I) employed in the compositions of the present invention contain, directly bonded to at least one aromatic group Ar, at least one group R which, independently, is an alkyl, alkenyl or aryl group containing at least 8 carbon atoms. More than one such group can be present, but usually no more than 2 or 3 are present for each aromatic nucleus in the aromatic group Ar.

The number of R groups on each Ar group is indicated by the the subscript m. For the purposes of this invention, each m may be independently an integer ranging from 1 up to about 10 with the proviso that m does not exceed the unsatisfied valences of the corresponding Ar. Frequently, each m is independently an integer ranging from 1 to about 3. In an especially preferred embodiment each m equals 1.

Each R frequently is an aliphatic group containing at least 8 and up to about 750 carbon atoms, frequently from 8 to about 600 carbon atoms, preferably from 8 to about 400 carbon atoms and more preferably from 8 to about 100 carbons. R is preferably alkyl or alkenyl, preferably substantially saturated alkenyl. In one preferred embodiment, R contains at least about 10 carbon atoms, often from 12 to about 100 carbons. In another embodiment, each R contains an average of at least about 30 carbon atoms, often an average of from about 30 to about 100 carbons. In another embodiment, R contains from 12 to about 50 carbon atoms. In a further embodiment, R contains from about 8 to about 24 carbon atoms, preferably from 12 to about 24 carbon atoms and more preferably from 12 to about 18 carbon atoms. In one embodiment, at least one R is derived from an alkane or alkene having number average molecular weight ranging from about 300 to about 800. In another embodiment, R contains an average of at least about 50 carbon atoms often from about 50 up to about 300, preferably up to about 100 carbon atoms.

When the group R is an alkyl or alkenyl group having from 8 to about 28 carbon atoms, it is typically derived from the corresponding olefin; for example, a dodecyl group is derived from dodecene, an octyl group is derived from octene, etc. When R is a hydrocarbyl group having at least about 30 carbon atoms, it is frequently an aliphatic group made from homo- or interpolymers (e.g., copolymers, terpolymers) of mono- and di-olefins having 2 to 10 carbon atoms, such as ethylene, propylene, butene-1, isobutene, butadiene, isoprene, 1-hexene, 1-octene, etc. Typically, these olefins are 1-mono olefins such as homopolymers of ethylene. These aliphatic hydrocarbyl groups may also be derived from halogenated (e.g., chlorinated or brominated) analogs of such homo- or interpolymers. R groups can, however, be derived from other sources, such as monomeric high molecular weight alkenes (e.g., 1-tetracontene) and chlorinated analogs and hydrochlorinated analogs thereof, aliphatic petroleum fractions, particularly paraffin waxes and cracked and chlorinated analogs and hydrochlorinated analogs thereof, white oils, synthetic alkenes such as those produced by the Ziegler-Natta process (e.g., poly(ethylene) greases) and other sources known to those skilled in the art. Any unsaturation in the R groups may be reduced or eliminated by hydrogenation according to procedures known in the art.

In one preferred embodiment, at least one R is derived from polybutene. In another preferred embodiment, R is derived from polypropylene. In a further preferred embodiment, R is a propylene tetramer.

As used herein, the term "hydrocarbyl group" denotes a group having a carbon atom directly attached to the remainder of the molecule and having predominantly hydrocarbon character within the context of this invention. Thus, the term "hydrocarbyl" includes hydrocarbon, as well as substantially hydrocarbon, groups, Substantially hydrocarbon describes groups, including hydrocarbon based groups, which contain non-hydrocarbon substituents, or non-carbon atoms in a ring or chain, which do not alter the predominantly hydrocarbon nature of the group.

Hydrocarbyl groups can contain up to three, preferably up to two, more preferably up to one, non-hydrocarbon substituent, or non-carbon heteroatom in a ring or chain, for every ten carbon atoms provided this non-hydrocarbon substituent or non-carbon heteroatom does not significantly alter the predominantly hydrocarbon character of the group. Those skilled in the art will be aware of such heteroatoms, such as oxygen, sulfur and nitrogen, or substituents, which include, for example, hydroxyl, halo (especially chloro and fluoro), alkoxyl, alkyl mercapto, alkyl sulfoxy, etc.

Examples of hydrocarbyl groups include, but are not necessarily limited to, the following:

(1) hydrocarbon groups, that is, aliphatic (e.g., alkyl or alkenyl), alicyclic (e.g., cycloalkyl, cycloalkenyl) groups, aromatic groups (e.g., phenyl, naphthyl), aromatic-, aliphatic- and alicyclic-substituted aromatic groups and the like as well as cyclic groups wherein the ring is completed through another portion of the molecule (that is, for example, any two indicated groups may together form an alicyclic radical);

(2) substituted hydrocarbon groups, that is, those groups containing non-hydrocarbon containing substituents which, in the context of this invention, do not significantly alter the predominantly hydrocarbon character; those skilled in the art will be aware of such groups (e.g., halo (especially chloro and fluoro), hydroxy, alkoxy, mercapto, alkylmercapto, nitro, nitroso, sulfoxy, etc.);

(3) hetero groups, that is, groups which will, while having a predominantly hydrocarbon character within the context of this invention, contain atoms other than carbon present in a ring or chain otherwise composed of carbon atoms. Suitable heteroatoms will be apparent to those of ordinary skill in the art and include, for example, sulfur, oxygen, nitrogen. Such groups as, e.g., pyridyl, furyl, thienyl, imidazolyl, etc. are representative of heteroatom containing cyclic groups.

Typically, no more than about 2, preferably no more than one, non-hydrocarbon substituent or non-carbon atom in a chain or ring will be present for every ten carbon atoms in the hydrocarbyl group. Usually, however, the hydrocarbyl groups are purely hydrocarbon and contain substantially no such non-hydrocarbon groups, substituents or heteroatoms.

Preferably, hydrocarbyl groups R are substantially saturated. By substantially saturated it is meant that the group contains no more than one carbon-to-carbon unsaturated bond, olefinic unsaturation, for every ten carbon-to-carbon bonds present. Usually, they contain no more than one carbon-to-carbon non-aromatic unsaturated bond for every 50 carbon-to-carbon bonds present. In an especially preferred embodiment, the hydrocarbyl group R is substantially free of carbon to carbon unsaturation. It is to be understood that, within the content of this invention, aromatic unsaturation is not normally considered to be olefinic unsaturation. That is, aromatic groups are not considered as having carbon-to-carbon unsaturated bonds.

Preferably, hydrocarbyl groups R of the anion containing groups of formula (II) of this invention are substantially aliphatic in nature, that is, they contain no more than one non-aliphatic (cycloalkyl, cycloalkenyl or aromatic) group for every 10 carbon atoms in the R group. Usually, however, the R groups contain no more than one such non-aliphatic group for every 50 carbon atoms, and in many cases, they contain no such non-aliphatic groups; that is, the typical R group is purely aliphatic. Typically, these purely aliphatic R groups are alkyl or alkenyl groups.

Specific non-limiting examples of substantially saturated hydrocarbyl R groups are: methyl, tetra (propylene), nonyl, triisobutyl, oleyl, tetracontanyl, henpentacontanyl, a mixture of poly(ethylene/propylene) groups of about 35 to about 70 carbon atoms, a mixture of the oxidatively or mechanically degraded poly(ethylene/propylene) groups of about 35 to about 70 carbon atoms, a mixture of poly (propylene/1-hexene) groups of about 80 to about 150 carbon atoms, a mixture of poly(isobutene) groups having between 20 and 32 carbon atoms, and a mixture of poly(isobutene) groups having an average of 50 to 75 carbon atoms. A preferred source of hydrocarbyl groups R are polybutenes obtained by polymerization of a $C_4$ refinery stream having a butene content of 35 to 75 weight percent and isobutene content of 15 to 60 weight percent in the presence of a Lewis acid catalyst such as aluminum trichloride or boron trifluoride. These polybutenes contain predominantly (greater than 80% of total repeating units) isobutene repeating units of the configuration

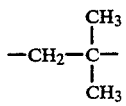

The attachment of a hydrocarbyl group R to the aromatic moiety Ar of the compounds of formula (I) of this invention can be accomplished by a number of techniques well known to those skilled in the art. One particularly suitable technique is the Friedel-Crafts reaction, wherein an olefin (e.g., a polymer containing an olefinic bond), or halogenated or hydrohalogenated analog thereof, is reacted with a phenol in the presence of a Lewis acid catalyst. Methods and conditions for carrying out such reactions are well known to those skilled in the art. See, for example, the discussion in the article entitled, "Alkylation of Phenols" in "Kirk-Othmer Encyclopedia of Chemical Technology", Third Edition, Vol. 2, pages 65–66, Interscience Publishers, a division of John Wiley and Company, New York, and U.S. Pat. Nos. 4,379,065; 4,663,063; and 4,708,809, all of which are expressly incorporated herein by reference for relevant disclosures regarding alkylation of aromatic compounds. Other equally appropriate and convenient techniques for attaching the hydrocarbon-based group R to the aromatic moiety Ar will occur readily to those skilled in the art.

The Groups Z

Each Z is independently OH, $(OR^4)_bOH$ or $O^-$ wherein each $R^4$ is independently a divalent hydrocarbyl group and b is a number ranging from 1 to about 30.

The subscript c indicates the number of Z groups that may be present as substituents on each Ar group. There will be at least one Z group substituent, and there may be more, depending on the value of the subscript m. For the purposes of this invention, c is a number ranging from 1 to about 3. In a preferred embodiment, c is 1.

As will be appreciated from the foregoing, the compounds of Formula I employed in this invention contain at least two Z groups and may contain one or more R groups as defined hereinabove. Each of the foregoing groups must be attached to a carbon atom which is a part of an aromatic nucleus in the Ar group. They need not, however, each be attached to the same aromatic nucleus if more than one aromatic nucleus is present in the Ar group.

As mentioned hereinabove, each Z group may be, independently, OH, $O^-$, or $(OR^4)_bOH$ as defined hereinabove. In a preferred embodiment, each Z is OH. In another embodiment, each Z may be $O^-$. In another preferred embodiment, at least one Z is OH and at least one Z is $O^-$. Alternatively, at least one Z may be a group of the Formula $(OR^4)_bOH$. As mentioned hereinabove, each $R^4$ is independently a divalent hydrocarbyl group. Preferably, $R^4$ is an aromatic or an aliphatic divalent hydrocarbyl group. Most preferably, $R^4$ is an alkylene group containing from 2 to about 30 carbon atoms, more preferably from 2 to about 8 carbon atoms and most preferably 2 or 3 carbon atoms.

The subscript b typically ranges from 1 to about 30, preferably from 1 to about 10, and most preferably 1 or 2 to about 5.

The Groups $R^1$, $R^2$ and $R^3$

Each of the groups $R^1$, $R^2$ and $R^3$ is independently H or a hydrocarbyl group. In one embodiment, each of $R^1$, $R^2$ and $R^3$ is, independently, H or a hydrocarbyl group having from 1 to about 100 carbon atoms, more often from 1 to about 24 carbon atoms. In a preferred embodiment, each of the aforementioned groups is independently hydrogen or alkyl or an alkenyl group. In one preferred embodiment each of $R^1$, $R^2$ and $R^3$ is, independently, H or lower alkyl. In an especially preferred embodiment, each of the aforementioned groups is H. For the purposes of this invention, the term "lower" when used to describe an alkyl or alkenyl group means from 1 to 7 carbon atoms.

The subscript x denotes the number of

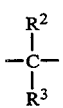

groups present in the anion containing group of Formula II. For the purposes of this invention, x normally ranges from 0 to about 8. In a preferred embodiment, x is 0, 1 or 2. Most preferably x equals 0.

The Group T

It will be apparent that when t=1 in any of Formula II, V or VI, that groups of Formulae V or VI will be present. Termination takes place when t=0. Thus, for example, when t=1 on Formula II, a group of Formula V or VI will be present. It follows then that in order for a group of Formula V or VI to be present in the anion containing group of formula II, t in formula II equals 1.

Likewise, when t=1 in formula II, a group of formula V or VI is present. When t in either formula V or VI equals 0, no further T groups are present. However, when t in formula V or VI equals 1, one or more additional T groups are present, terminating only when finally t=0.

In one preferred embodiment, t in formula II equals zero and no groups of formula V or VI are present. In another preferred embodiment, t in formula II equals 1 and from 1 up to about 3, preferably up to 2 additional groups T of formula V or VI are present.

The Metal Ions M

The symbol M in Formula I represents one or more metal ions. These include alkali metal, alkaline earth metals, zinc, cadmium, lead, cobalt, nickel, iron, manganese, copper and others. Preferred are the alkali and alkaline earth metals. Especially preferred are sodium, potassium, calcium, and lithium. Most preferred are sodium and lithium.

The metal ions M may be derived from reactive metals or reactive metal compounds that will react with carboxylic acids or phenols to form carboxylates and phenates. The metal salts may be prepared from reactive metals such as alkali metals, alkaline earth metals, zinc, lead, cobalt, nickel, iron and the like. Examples of reactive metal compounds are sodium oxide, sodium hydroxide, sodium carbonate, sodium methylate, sodium phenoxide, corresponding potassium and lithium compounds, calcium oxide, calcium hydroxide, calcium carbonate, calcium methylate, calcium chloride, calcium phenoxide, and corresponding barium and magnesium compounds, zinc oxide, zinc hydroxide, zinc carbonate, cadmium chloride, lead oxide, lead hydroxide, lead carbonate, nickel oxide, nickel hydroxide, nickel nitrate, cobalt oxide, ferrous carbonate, ferrous oxide, cupric acetate, cupric nitrate, etc.

The above metal compounds are merely illustrative of those useful in this invention and the invention is not to be considered as limited to such. Suitable metals and metal-containing reactants are disclosed in many U.S. Patents including U.S. Pat. Nos. 3,306,908; 3,271,310; and U.S. Pat. No. RE. 26,433.

The Total Valence y

The skilled worker will appreciate that the compounds of the general formula $$A^{y-}M^{y+} \qquad (I)$$

constitute a substantially neutral metal salt, which metal salt is a carboxylate and/or phenate, depending on the nature of A. Depending on the nature of the group Z in Formula (II), A may be a carboxylate, or a carboxylate-phenate, a carboxylate-mixed phenate/phenol, a carboxylate-alkoxylate, a carboxylate-phenate-alkoxylate, a carboxylate-phenate/phenol-alkoxylate, etc. The group A may also represent mixtures of two or more of these. Accordingly, it is apparent that the value of y is dependent upon the number of anion-containing moieties making up A and on the valence of the metal ion M.

Preferably, salts of Formula I are neutral salts. However, it is to be understood that salts of formula I comprising up to about 50% unreacted carboxylic acid groups or lactone are also contemplated as being within the scope of this invention. Preferably, the salt of Formula(I) comprises no more than about 30% unreacted carboxylic acid groups or lactone, more preferably, no more than about 15% and even more preferably, no more than about 5% unreacted carboxylic acid or lactone.

It is also to be understood that the salts of Formula (I) may also be slightly basic, that is, they may contain a small excess of metal beyond that which is normally expected based on the stoichiometry of the components making up Formula (I). Preferably, no more than 25% excess metal, more preferably no more than 15% and even more preferably, no more than 5% excess metal is incorporated into the salt of Formula (I).

As was indicated hereinabove, especially preferred and normally, the salt of Formula (I) is substantially neutral, that is, the amount of metal is no more than about 1% above or below that normally expected based on the stoichiometry of the components of the salt of Formula (I).

The metal salts of Formula (I) of this invention may be readily prepared by reacting (a) a reactant of the formula $$R_m-Ar-Z_c \qquad (III)$$
$$\quad | \quad$$
$$(H)_s$$

wherein R is alkyl, alkenyl or aryl containing at least 8 carbon atoms, m ranges from 1 to about 10, Ar is an aromatic group containing from 4 to about 30 carbon atoms having from 0 to 3 optional substituents selected as described hereinabove, or an analog of such an aromatic nucleus, wherein s is an integer of at least 1 and wherein the total of s+m does not exceed the available valences of Ar and Z is selected from the group consisting of OH or $(OR^4)_bOH$ wherein each $R^4$ is independently a divalent hydrocarbyl group and b is a number ranging from 1 to about 30 and c ranges from 1 to about 3, with (b) a carboxylic reactant of the formula $$R^1CO(CR^2R^3)_xCOOR^6 \qquad (IV)$$

wherein $R^1$, $R^2$ and $R^3$ are independently H or a hydrocarbyl group, $R^6$ is H or an alkyl group, and x is an integer ranging from 0 to about 8 and then reacting the intermediate so formed with a metal-containing reactant to form a salt.

When $R^1$ is H, the aldehyde moiety of reactant (IV) may be hydrated. For example, glyoxylic acid is readily available commercially as the hydrate having the formula $$(HO)_2CH-COOH.$$

Water of hydration as well as any water generated by the condensation reaction is preferably removed during the course of the reaction.

Ranges of values and descriptions of the groups and subscripts appearing in the above Formulae (III) and (IV) are the same as recited hereinabove for Formulae (I) and (II). When $R^6$ is an alkyl group it is preferably a lower alkyl group, most preferably, ethyl or methyl.

The reaction is normally conducted in the presence of a strong acid catalyst. Particularly useful catalysts are illustrated by methanesulfonic acid and para-toluenesulfonic acid. The reaction is usually conducted with the removal of water.

Reactants (a) and (b) are preferably present in a molar ration of about 2:1; however, useful products may be obtained by employing an excess amount of either reactant. Thus, molar ratios of (a):(b) of 1:1, 2:1, 1:2, 3:1, etc. are contemplated and useful products may be obtained thereby. Illustrative examples of reactants (a) of Formula (III) include hydroxy aromatic compounds such as phenols, both substituted and unsubstituted within the constraints imposed on Ar hereinabove, alkoxylated phenols such as those prepared by reacting a phenolic compound with an epoxide, and a variety of aromatic hydroxy compounds. In all the above cases, the aromatic groups bearing the phenolic —OH or $(OR^4)_bOH$ groups may be single ring, fused ring or linked aromatic groups as described in greater detail hereinabove.

Specific illustrative examples of compound (III) employed in the preparation of compounds of Formula (I) containing the anion containing groups A of Formula (II) include hydrocarbon substituted-phenol, naphthol, 2,2'-dihydroxybiphenyl, 4,4-dihydroxybiphenyl, 3-hydroxyanthracene, 1,2,10-anthracenetriol, resorcinol, 2-t-butyl phenol, 4-t-butyl phenol, 2,6-di-t-butyl phenol, octyl phenol, cresols, propylene tetramer-substituted phenol, propylene oligomer (MW 300–800)-substituted phenol, polybutene ($M_n$ about 1000) substituted phenol substituted naphthols corresponding to the above exemplified phenols, methylene-bis-phenol, bis-(4-hydroxyphenyl)-2,2-propane, and hydrocarbon substituted bisphenols wherein the hydrocarbon substituents have at least 8 carbon atoms for example, octyl, dodecyl, oleyl, polybutenyl, etc., sulfide-and polysulfide-linked analogues of any of the above, alkoxylated derivatives of any of the above hydroxy aromatic compounds, etc. Preferred compounds of Formula (III) are those that will lead to the compounds of Formula (I) having preferred anion containing groups of Formula (II).

The method of preparation of numerous alkyl phenols is well-known. Illustrative examples of alkyl phenols and related aromatic compounds and methods for preparing same are give in U.S. Pat. No. 4,740,321 to Davis et al. This patent is hereby incorporated herein by reference.

Non-limiting examples of the carboxylic reactant (b) of Formula IV include glyoxylic acid and other omega-oxoalkanoic acids, keto alkanoic acids such as pyruvic acid, levulinic acid, ketovaleric acids, ketobutyric acids and numerous others. The skilled worker will readily recognize the appropriate compound of Formula (IV) to employ as a reactant to generate a given anion-containing group A. Preferred compounds of Formula (IV) are those that will lead to compounds of Formula (I) having preferred anion containing groups of Formula (II).

U.S. Pat. Nos. 2,933,520 (Bader) and 3,954,808 (Elliott et al) describe procedures for preparing the intermediate via reaction of phenol and acid. These patents are expressly incorporated herein for relevant disclosures contained therein.

The intermediate product obtained from the reaction of the foregoing hydroxy aromatic compounds and carboxylic acids is then reacted with a metal containing reactant to form a salt. Suitable metal containing reactants have been enumerated hereinabove.

The above examples are intended to be illustrative of suitable reactants and are not intended, and should not be viewed as, an exhaustive listing thereof.

It will be appreciated that the reaction of reactants (a) and (b) will lead to a compound containing a group Z which may be —OH or $(OR^4)_bOH$, as described hereinabove except that when the product is a lactone, Z may be absent. Furthermore, a phenolic group containing product may be reacted with, for example, an epoxide, to generate —$(OR^4)OH$ groups, either on the intermediate arising from reaction of (a) and (b) or of a salt thereof.

The intermediate arising from the reaction of (a) and (b) may be a carboxylic acid or a lactone, depending upon the nature of (a). In particular, when (a) is a highly hindered hydroxy aromatic compound, the product from (a) and (b) is usually a carboxylic acid. When the hydroxy aromatic reactant (a) is less hindered, a lactone is generated.

Often, the intermediate arising from the reaction of (a) and (b) is a mixture comprising both lactone and carboxylic acid.

When the intermediate from (a) and (b) is further reacted with the metal-containing reactant, generally a carboxylic acid salt is formed first. If an excess of metal reactant is used, an amount beyond that needed for formation of a carboxylic acid salt, further reaction takes place at aromatic —OH groups.

From time to time it has been noted that before all lactone is converted to carboxylic acid salt, the beginning of conversion of phenolic —OH groups to O$^-$ groups, i.e., phenate salts, is observed. This appears to occur most often when the metal reactant is a calcium reactant.

The carboxylate salt forms by reaction of the metal containing reactant with the lactone, opening the lactone ring, forming a carboxylate salt, or from direct reaction with a carboxylic acid group. It is generally preferred to utilize sufficient metal-containing reactant to substantially neutralize all of the carboxylic acid; however, conversion of at least 50%, more preferably 75% of lactone or carboxylic acid to carboxylic acid salt is desirable. Preferably, at least 90%, more preferably 99–100% conversion of lactone or carboxylic acid to carboxylic acid salt is effected.

The following specific illustrative Examples describe the preparation of the compounds of Formula (I) useful in the compositions of this invention. In the following examples, as well as in the claims and in the specification of this application, parts are parts by weight, the temperature is degrees Celsius and the pressure is atmospheric, unless otherwise indicated.

As will be readily apparent to those skilled in the art, variations of each of the illustrated reactants and combinations of reactants and conditions may be used.

EXAMPLE 1

A mixture is prepared by combining 3317 parts of a polybutene-substituted phenol prepared by boron trifluoride-phenol catalyzed alkylation of phenol with a polybutene having a number average molecular weight of approximately 1,000 (vapor phase osmometry), 218 parts 50% aqueous glyoxylic acid (Aldrich Chemical) and 1.67 parts 70% aqueous methanesulfonic acid in a reactor equipped with a stirrer, thermo-well, subsurface gas inlet gas inlet and a Dean-Stark trap with condenser for water removal. The mixture is heated under a nitrogen flow to a temperature of 160° C. over one hour. The reaction is held at 160° C. for four hours with removal of water; a total of 146 parts aqueous distillate is collected. Mineral oil diluent, 2284 parts, is added with stirring followed by cooling of the reaction mixture to room temperature. At room temperature, 117.6 parts 50% aqueous sodium hydroxide and 500 parts water are added with stirring followed by exothermic reaction to about 40° C. over 10 minutes. The Dean-Stark trap is removed and the condenser is arranged to allow for reflux. The mixture is heated over one hour to a temperature of 95° C. and is held at this temperature for three hours. The reaction mixture is then cooled to about 60° C. and stripping is started by applying a vacuum to reduce the pressure to about 100 millimeters mercury. The pressure is slowly decreased and the temperature is increased over a period of approximately eight hours until the temperature is 95° C. and the pressure is 20 millimeters mercury. The reaction is then held at this temperature and pressure for three hours to complete stripping. The residue is filtered through a diatomaceous earth filter aid at a temperature of about 95° C. The resulting product, containing approximately 40% mineral oil diluent has a sodium content of 0.58%, ASTM color (D1500) of 7.0 (neat), and a total base number of 13.2. The infra-red spectrum of the product is substantially free of absorption at 1790 cm$^{-1}$ indicating absence of lactone carbonyl.

EXAMPLE 2

A reactor is charged with 3537 parts of a propylene tetramer-substituted phenol prepared by alkylation of phenol with a propylene tetramer in the presence of a sulfonated polystyrene catalyst (marketed as Amberlyst-15 by Rohm & Haas Company), 999 parts of 50% aqueous glyoxylic acid (Hoechst Celanese) and 3.8 parts 70% aqueous methane sulfonic acid. The reaction is heated to 160° C. over three hours under a nitrogen flow. The reaction is held at 160° C. for four hours while collecting 680 parts water in a Dean-Stark trap.

A mineral oil diluent, 2710 parts, is added in one portion with stirring and the reaction is cooled to room temperature. At room temperature, 540 parts 50% aqueous sodium hydroxide and 1089 parts water are added quickly with stirring followed by an exothermic reaction to about 54° C. over ten minutes. The Dean-Stark trap is removed and the condenser is arranged to allow for reflux. The reaction mixture is heated to 95°-100° C. and held at this temperature range for three hours. The mixture is then cooled to 60° C. and a vacuum is applied until the pressure reaches 100 millimeters mercury. Vacuum stripping of water is begun while the temperature is slowly increased to 95°-100° C. over seven hours while reducing pressure to 20 millimeters mercury. Stripping is continued at 95°-100° C. at 20 millimeters mercury pressure for three hours. The residue is filtered through a diatomaceous earth filter aid at 90°-100° C. A product containing approximately 40% diluent oil is obtained containing, by analysis, 2.18% sodium and which has an ASTM color (D-1500) of 6.5. The infrared spectrum shows no significant absorption at 1790 cm$^{-1}$ indicating the product contains no lactone carbonyl.

EXAMPLE 3

A mixture of 681 parts of a polyisobutene substituted phenol-glyoxylic acid reaction product prepared according to the procedure of Example 1, 11 parts calcium hydroxide, 461 parts of mineral oil and 150 parts of water are charged to a reactor and heated under a nitrogen blanket at 100°-105° C. for four hours. The reaction mixture is stripped at 115°-120° C. at five millimeters mercury pressure over four hours. The residue is filtered at 115°-120° C. employing a diatomaceous earth filter aid. The filtered product containing approximately 40% diluent oil contains, by analysis, 0.42% calcium and has a total base number of 15.1. The infrared spectrum of the product shows a weak absorption at 1778 cm$^{-1}$ indicating a trace of lactone in the product.

EXAMPLE 4

A reactor is charged with 655 parts of a propylene tetramer-substituted phenol prepared according to the procedure given in Example 2, 185 parts 50% aqueous glyoxylic acid (Aldrich) and 0.79 parts 70% aqueous methanesulfonic acid. The flask is equipped with a subsurface nitrogen inlet, a stirrer, thermo-well and Dean-Stark trap for the collection of water. The materials are heated to 120° C. over three hours. 119 parts water is collected (theory=137.5 parts). Mineral oil diluent (490 parts) is added in one increment followed by cooling to 60° C. At 60° C., 52.5 parts lithium hydroxide monohydrate is added. No exothermic reaction is noted. The reaction mixture is heated to 95° C. for one hour. At this point the infra-red shows substantially no lactone absorption. Heating at 95° C. is continued for an additional two hours, followed by vacuum stripping to 95° C. at 25 millimeters mercury for three hours. The residue is filtered through diatomaceous earth filter aid. The dark orange liquid contains 5.02% sulfate ash which indicates 0.63% lithium content. The product has a total base number of 59.

EXAMPLE 5

A reactor is charged with 2500 parts of a propylene tetramer-substituted phenol prepared according to the procedure given in Example 2, 706 parts 50% aqueous glyoxylic acid (Aldrich) and 4.75 parts paratoluene sulfonic acid monohydrate (Eastman) and 650 parts toluene. The materials are heated under nitrogen at reflux (maximum temperature 140° C.) for 10 hours; 490 parts water is collected using a Dean-Stark trap. The reaction product is stripped to 130° C. at 20 millimeters mercury pressure over three hours. Mineral oil diluent (1261 parts) is added and the product is filtered through diatomaceous earth filter aid at 100° C. The infra-red spectrum shows an absorbance at 1795 cm$^{-1}$ indicating the presence of lactone. Another reactor is charged with 500 parts of this lactone-containing product, 48.4 parts 50% aqueous sodium hydroxide, 100 parts water and 83 parts mineral oil diluent. The materials are reacted under nitrogen at 95°-100° C. for ten hours. The reaction mixture is vacuum stripped to 120° C. at 20 millimeters mercury pressure over three hours. The residue is filtered through a diatomaceous earth filter aid at 100°-120° C. The filtered product shows 2.36% sodium, by analysis. The infra-red spectrum shows no carbonyl absorption at 1795 cm$^{-1}$.

EXAMPLE 6

A reactor is charged with 2849 parts of a polypropylene substitued phenol prepared by alkylation of phenol with a polypropylene having a molecular weight of about 400 in the presence of a boron trifluoride-ether catalyst, 415 parts of 50% aqueous glyoxylic acid (Aldrich) and 4 parts of paratoluenesulfonic acid monohydrate (Eastman). The reactants are heated under nitrogen to 155°–160° C. over three hours. Heating is continued at 155°–160° C. for four hours. A total of 278 parts water is collected employing a Dean-Stark trap.

Another reactor is charged with 600 parts of the above-described product, 91 parts of 50% aqueous sodium hydroxide, about 347 parts toluene and 424 parts mineral oil. The materials are heated at reflux (maximum temperature-125° C.) for six hours. 54.5 parts water is collected using a Dean-Stark trap. The reaction mixture is stripped to 120° C. at 30 millimeters mercury pressure over three hours. The residue is filtered employing a diatomaceous earth filter aid at 110°–120° C. The residue contains, by analysis, 2% sodium. The infra-red spectrum shows no lactone carbonyl absorption at 1795 cm$^{-1}$.

EXAMPLE 7

A reactor is charged with 700 parts of the polypropylene substituted phenol-glyoxylic acid reaction product described in Example 6, 24.5 parts calcium hydroxide, about 100 parts water and 483 parts mineral oil. The materials are heated under nitrogen to 95°–100° C. and held at that temperature for eight hours. The infra-red spectrum at this point indicates lactone has been consumed. The materials are vacuum stripped to 100°–105° C. at 20 millimeters mercury pressure over two hours. The residue is filtered at 100°–105° C. employing a diatomaceous earth filter aid. The filtrate contains, by analysis, 0.934% calcium. The infra-red spectrum shows that a small amount of lactone remains.

Example 8

A reactor is charged with 528 parts of a propylene-tetramer substituted phenol-glyoxylic acid reaction product prepared in the same manner described in Example 4, 18.5 parts sodium hydroxide, about 433 parts toluene and 40 parts water. The materials are heated under nitrogen at 85° C. (reflux) for four hours. Barium chloride dihydrate (Eastman) (56 parts) is added and the materials are heated at reflux for four hours followed by removal of water employing a Dean-Stark trap over three hours. The materials are cooled and solids are removed by filtration. The filtrate is stripped to 150° C. at 15 millimeters mercury pressure. The residue contains, by analysis, 2.82% barium and 1.01% sodium. The infra-red spectrum shows a weak lactone absorption.

EXAMPLE 9

A mixture is prepared by combining 680 parts of a polybutene-substituted phenol such as described in Example 1, 44.7 parts 50% aqueous glyoxylic acid (Aldrich) and 0.34 parts methanesulfonic acid in a reactor equipped with a subsurface gas inlet, thermowell, stirrer, and Dean-Stark trap with condenser. The materials are heated to 120° C. and held at that temperature for three hours; 24 parts water is collected. Mineral oil, 466 parts, is added followed by cooling of the materials to 73° C. A solution of 12.68 parts lithium hydroxide monohydrate is dissolved in 50 parts water. This solution is added to the reactor at 73° C. No exothermic reaction is noted. The Dean-Stark trap is removed and the condenser is replaced. The materials are heated to 95° C. and are held at that temperature for two hours. The materials are stripped at 95° C. at 20 millimeters mercury pressure for two hours. The residue is filtered through a diatomaceous earth filter aid at 95° C. The filtrate contains, by analysis, 0.51% lithium and 1.20% sulfate ash and has a total base number of 13.55. The ASTM color (D-1500 procedure) is 5.5.

EXAMPLE 10

A reactor is charged with 420 parts of a propylene-tetramer substituted phenol-glyoxylic acid reaction product prepared according to the procedure given in Example 4, 31 parts potassium hydroxide and about 260 parts toluene. The materials are heated under nitrogen to 120° C. and held at 120°–130° C. for four hours. Following reaction, the infra-red spectrum shows no lactone remains. Naphthenic oil diluent (660 parts) is added followed by stripping to 140° C. at 2 millimeters mercury pressure for three hours. The residue is filtered through a diatomaceous earth filtrate at 130°–140° C. The filtrate contains, by analysis, 1.47% potassium and has a total base number of 21.6.

EXAMPLE 11

The reactor is charged with 350 parts of the potassium salt described in Example 10, 55 parts zinc chloride, about 350 parts xylene and 80 parts water. The materials are heated to reflux (90°–95° C.) under nitrogen. Heating is continued at 90°–95° C. for 10 hours. Water is removed as an azeotrope employing a Dean-Stark trap. Following reaction, solids are removed by filtration. The filtrate is stripped under vacuum. The residue contains, by analysis, 0.27% zinc and 0% potassium. The infra-red spectrum shows the presence of an undetermined amount of lactone.

EXAMPLE 12

A reactor is charged with 130 parts of a propylene tetramer substituted phenol-glyoxylic acid reaction product prepared as described in Example 2, 8.2 parts of potassium hydroxide, 10 parts water and 130 parts xylene. The materials are heated under nitrogen at 90° for three hours. Barium chloride dihydrate (16 parts) is added and the reactants are heated at reflux under nitrogen for five hours. Following the heating period water is removed using a Dean-Stark trap. The mixture is cooled and filtered. The filtrate is stripped under vacuum on a rotary evaporator. The residue contains, by analysis, 2.91% barium and 2.04% potassium. The neutralization number employing bromphenol blue indicator is 28.8.

EXAMPLE 13

A reactor is charged with 700 parts of the polypropylene substituted phenol-glyoxylic acid reaction product described in Example 6, 53 parts 50% aqueous sodium hydroxide, 100 parts water and 484 parts mineral oil. The materials are heated under nitrogen at 95°–100° C. for five hours. The reaction mixture is stripped to 120° C. at 20 millimeters mercury pressure for three hours. The residue is filtered employing a diatomaceous earth filter aid.

EXAMPLE 14

A reactor is charged with 500 parts of a propylene tetramer substituted phenol-glyoxylic acid reaction product prepared in a fashion similar to that as described in Example 4, but containing about 32% by weight mineral oil diluent, 22.4 parts calcium hydroxide, 100 parts water and 82 parts mineral oil. The reaction mixture is heated under nitrogen at reflux (95°–100° C.) for twelve hours. At this point the infra-red shows substantially no lactone carbonyl absorption. The reaction mixture is stripped to 100° C. at 20 millimeters mercury pressure for three hours. The residue is filtered at 95°-100° C. employing a diatomaceous earth filter aid.

EXAMPLE 15-21

Reaction products are prepared substantially according to the procedure of Example 1, replacing the polybutene substituted phenol with an equivalent amount, based on the molecular weight, of the alkylated hydroxy aromatic compounds listed in the following Table I

TABLE I

| Example | Name | Mol. Wt.[1] |
|---|---|---|
| 15 | 2,2'-dipoly(isobutene)yl-4,4'-dihydroxybiphenyl | 2500 |
| 16 | 8-hydroxy-poly(propene)yl-1-azanaphthalene | 900 |
| 17 | 4-poly(isobutene)yl-1-naphthol | 1700 |
| 18 | 2-poly(propene/butene-1)yl-4,4'-isopropylidene-bisphenol[2] | 3200 |
| 19 | 4-tetra(propene)yl-2-hydroxyanthracene | — |
| 20 | 4-octadecyl-1,3-dihydroxybenzene | — |
| 21 | 4-poly(isobutene)-3-hydroxypyridine | 1300 |

[1]Number average molecular weight by vapor phase osmometry
[2]The molar ratio of propene to butene-1 in the substituent is 2:3

EXAMPLE 22

The procedure of Example 3 is repeated except the polybutene has an average molecular weight of about 1400.

EXAMPLE 23

The procedure of Example 9 is repeated employing a substituted phenol (having an —OH content of 1.88%, prepared by reacting polyisobutenyl chloride having a viscosity at 99° C. of 1306 SUS (Sayboldt Universal Seconds) and containing 4.7% chlorine with 1700 parts phenol).

EXAMPLE 24

The procedure of Example 14 is repeated replacing the propylene tetramer substituted phenol with an equivalent number of moles of a sulfurized alkylated phenol prepared by reacting 1000 parts of a propylene tetramer substituted phenol as described in Example 2 with 175 parts of sulfur dichloride and diluted with 400 parts mineral oil.

EXAMPLE 25

The procedure of Example 24 is repeated replacing the sulfurized phenol with a similar sulfurized phenol prepared by reacting 1000 parts of propylene tetramer substituted phenol with 319 parts of sulfur dichloride.

EXAMPLE 26

The procedure of Example 2 is repeated replacing glyoxylic acid with an equivalent amount, based on —COOH, of pyruvic acid.

EXAMPLE 27

The procedure of Example 6 is repeated replacing glyoxylic acid with an equivalent amount , based on —COOH, of levulinic acid.

EXAMPLES 28-30

The procedure of Example 3 is repeated employing the keto alkanoic acids given in Table II.

TABLE II

| Example | Acid |
|---|---|
| 28 | Pyruvic |
| 29 | 3-Ketobutyric |
| 30 | Keto valeric |

EXAMPLE 31

The procedure of Example 4 is repeated replacing glyoxylic acid with an equivalent amount, based on —COOH, of omega-oxo-valeric acid.

EXAMPLES 32-35

The procedures of each of Examples 1-4 is repeated replacing the alkylated phenol with a propylene tetramer-substituted catechol.

EXAMPLE 36

A reactor equipped with a subsurface gas inlet, stirrer, thermowell and Dean-Stark trap with condenser is charged with 676 parts of polybutene substituted phenol prepared as described in Example 1, 44 parts 50% aqueous glyoxylic acid, and 0.34 parts methanesulfonic acid. The materials are heated to 120° C. and held there for 3.5 hours while collecting 27 parts $H_2O$ (34 parts theory). Mineral oil diluent (467 parts) is added, the materials are cooled to 72° C. and a solution of 19.8 parts 85% KOH in 50 parts $H_2O$ is added. The Dean-Stark trap is removed, the condenser is replaced. A slight exotherm (about 1° C.) is observed. The materials are heated to 95° C. and held there for 2 hours. The materials are stripped to 95° C. at 20 mm Hg pressure and filtered employing a diatomaceous earth filter aid. The filtrate contains, by analysis, 0.85% K and 1.20% $SO_4$ ash. The total base number is 12.0. ASTM Color (D-1500)=6.0 neat, 8.0 dilute.

EXAMPLE 37

A reactor is charged with 318 parts of a polybutene-substituted phenol as described in Example 1, 0.16 parts 70% aqueous methanesulfonic acid and 31.5 parts of 50% aqueous glyoxylic acid (Aldrich). The materials are heated at 125°-130° C. for 6 hours while collecting 21.5 parts water in a Dean-Stark trap. Mineral oil diluent (223.1 parts) is added and the materials are cooled to room temperature. To this oil solution is added 17 parts 50% aqueous NaOH. An exothermic reaction is observed. The materials are heated for 3 hours at 100°-105° C., then vacuum stripped at 110°-120° C., 20 mm Hg pressure, for 4 hours. The residue is filtered employing a diatomaceous earth filter aid.

EXAMPLE 38

A reactor is charged with 997 parts of the polybutene-substituted phenol as described in Example 1, 75.4 parts of 50% aqueous glyoxylic acid and 0.5 parts of methanesulfonic acid. The materials are heated at 120° C. for 4.5 hours while collecting 40 parts water in a Dean-Stark trap. The materials are then vacuum stripped to 120° C. at 20 mm Hg, removing an additional 5 parts aqueous distillate.

To another reactor is charged 450 parts of the above-described product, 15.7 parts 50% aqueous NaOH and 305 parts mineral oil diluent. The materials are heated with nitrogen purging at 95°–100° C. for 3 hours followed by vacuum stripping to 100° C. at 20 mm Hg and filtering through a diatomaceous earth filter aid. The filtrate contains, by analysis, 0.444% Na. The infrared spectrum shows a detectable absorption at 1788 cm$^{-1}$. The total base number is 11.5.

EXAMPLE 39

Following substantially the procedure of Example 38, 431 parts of the phenol-glyoxylic acid product described in that example and 17.3 parts 50% aqueous NaOH in 293 parts mineral oil diluent are reacted to form a product containing, by analysis, 0.64% sodium. The infrared spectrum shows no detectable absorption at 1788 cm$^{-1}$. The total base number is 14.6.

EXAMPLE 40

To a 5-liter flask are added 2182 parts of the alkyl phenol described in Example 1, 143.4 parts 50% aqueous glyoxylic acid and 1.1 parts 70% methane sulfonic acid followed by heating under N$_2$ to 155°–160° C. over 3 hours. The temperature is maintained at 155°–160° C. for 2 hours; 92 parts aqueous distillate is collected (theory 107 parts) in a Dean-Stark trap. Diluent oil (1533 parts) is added and the materials are cooled to 27° C. Sodium hydroxide (50% aqueous, 155 parts) is added and the materials are heated to 110° C. and held at 110°–120° C. for 2 hours. The materials are cooled to 50° C. then vacuum stripped over 4 hours to 110° C. at 20 mm Hg pressure. The residue is filtered employing a diatomaceous earth filter aid. The product contains, by analysis, 1.16% Na and has a total base number of 27.2.

As previously indicated, the metal salts of this invention are useful as additives in preparing lubricant compositions where they function to improve, for example, detergency, dispersancy, anti-rust, antioxidancy and the like.

The lubricating oil compositions of this invention are based on natural and synthetic lubricating oils and mixtures thereof. These lubricants include crankcase lubricating oils for spark-ignited and compression-ignited internal combustion engines, such as automobile and truck engines, marine and railroad diesel engines, and the like. Automatic transmission fluids, transaxle lubricants, gear lubricants, metal-working lubricants, hydraulic fluids and other lubricating oil and grease compositions can also benefit from the incorporation therein of the metal salts of this invention.

In general, about 0.05–30, usually about 0.1–15 parts (by weight) of at least one metal salt of this invention is dissolved or stably dispersed in 100 parts of oil to produce a satisfactory lubricant.

In addition to the metal salts of Formula I the use of other additives is contemplated.

It is sometimes useful to incorporate, on an optional, as-needed basis, other known additives which include, but are not limited to, dispersants and detergents of the ash-producing or ashless type, antioxidants, anti-wear agents, extreme pressure agents, emulsifiers, demulsifiers, foam inhibitors, friction modifiers, anti-rust agents, corrosion inhibitors, viscosity improvers, pour point depressants, dyes, lubricity agents, and solvents to improve handleability which may include alkyl and/or aryl hydrocarbons. These optional additives may be present in various amounts depending on the intended application for the final product or may be excluded therefrom.

The ash-containing detergents are the well-known neutral or basic Newtonian or non-Newtonian, basic salts of alkali, alkaline earth and transition metals with one or more hydrocarbyl sulfonic acid, carboxylic acid, phosphoric acid, mono- and/or dithio phosphoric acid, phenol or sulfur coupled phenol, and phosphinic and thiophosphinic acid. Commonly used metals are sodium, potassium, calcium, magnesium, lithium, copper and the like. Sodium and calcium are most commonly used.

Neutral salts contain substantially equivalent amounts of metal and acid. As used herein, the expression basic salts refers to those compositions containing an excess amount of metal over that normally required to neutralize the acid substrate. Such basic compounds are frequently referred to as overbased, superbased, etc.

Dispersants include, but are not limited to, hydrocarbon substituted succinimides, succinamides, carboxylic esters, Mannich dispersants and mixtures thereof as well as materials functioning both as dispersants and viscosity improvers. The dispersants include nitrogen-containing carboxylic dispersants, ester dispersants, Mannich dispersants or mixtures thereof. Nitrogen-containing carboxylic dispersants are prepared by reacting a hydrocarbyl carboxylic acylating agent (usually a hydrocarbyl substituted succinic anhydride) with an amine (usually a polyamine). Ester dispersants are prepared by reacting a polyhydroxy compound with a hydrocarbyl carboxylic acylating agent. The ester dispersant may be further treated with an amine. Mannich dispersants are prepared by reacting a hydroxy aromatic compound with an amine and aldehyde. The dispersants listed above may be post-treated with reagents such as urea, thiourea, carbon disulfide, aldehydes, ketones, carboxylic acids, hydrocarbon substituted succinic anhydride, nitriles, epoxides, boron compounds, phosphorus compounds and the like. These dispersants are generally referred to as ashless dispersants even though they may contain elements such as boron or phosphorus which, on decomposition, will leave a non-metallic residue.

Extreme pressure agents and corrosion- and oxidation-inhibiting agents include chlorinated compounds, sulfurized compounds, phosphorus containing compounds including, but not limited to, phosphosulfurized hydrocarbons and phosphorus esters, metal containing compounds and boron containing compounds.

Chlorinated compounds are exemplified by chlorinated aliphatic hydrocarbons such as chlorinated wax.

Examples of sulfurized compounds are organic sulfides and polysulfides such as benzyl disulfide, bis(chlorobenzyl)disulfide, dibutyl tetrasulfide, sulfurized methyl ester of oleic acid, sulfurized alkylphenol, sulfurized dipentene, and sulfurized terpene.

Phosphosulfurized hydrocarbons include the reaction product of a phosphorus sulfide with turpentine or methyl oleate.

Phosphorus esters include dihydrocarbon and trihydrocarbon phosphites, phosphates and metal and amine salts thereof.

Phosphites may be represented by the following formulae:

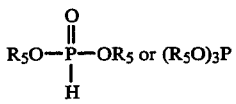

wherein each $R_5$ is independently hydrogen or a hydrocarbon based group, provided at least one $R_5$ is a hydrocarbon based group.

Phosphate esters include mono-, di- and trihydrocarbon-based phosphates of the general formula $(R_5O)_3PO.$ Examples include mono-, di- and trialkyl; mono-, di and triaryl and mixed alkyl and aryl phosphates.

Metal containing compounds include metal thiocarbamates, such as zinc dioctyldithiocarbamate, and barium heptylphenyl dithiocarbamate, molybdenum compounds, organodithiophosphate salts such as zinc, copper, manganese, etc., salts.

Boron containing compounds include borate esters and boron-nitrogen containing compounds prepared, for example, by the reaction of boric acid with a primary or secondary alkyl amine.

Viscosity improvers include, but are not limited to, polyisobutenes, polymethacrylate acid esters, polyacrylate acid esters, diene polymers, polyalkyl styrenes, alkenyl aryl conjugated diene copolymers, polyolefins and multifunctional viscosity improvers.

Pour point depressants are a particularly useful type of additive often included in the lubricating oils described herein. See for example, page 8 of "Lubricant Additives" by C. V. Smalheer and R. Kennedy Smith (Lesius-Hiles Company Publishers, Cleveland, Ohio, 1967).

Diluents include such materials as high boiling petroleum naphthas, mineral oil, etc. When used, they are typically present in amounts ranging from about 5% to about 25% by weight.

Anti-foam agents used to reduce or prevent the formation of stable foam include silicones or organic polymers. Examples of these and additional anti-foam compositions are described in "Foam Control Agents", by Henry T. Kerner (Noyes Data Corporation, 1976), pages 125–162.

These and other additives are described in greater detail in U.S. Pat. No. 4,582,618 (column 14, line 52 through column 17, line 16, inclusive), herein incorporated by reference for its disclosure of other additives that may be used in the compositions of the present invention.

The components may be blended together in any suitable manner and then admixed, for example with a diluent to form a concentrate as discussed below, or with a lubricating oil, as discussed below. Alternatively, components can be admixed separately with such diluent or lubricating oil. The blending technique for mixing the components is not critical and can be effected using any standard technique, depending upon the specific nature of the materials employed. In general, blending can be accomplished at room temperature; however, blending can be facilitated by heating the components.

As previously indicated, the compositions of the present invention are useful as additives for lubricants. They can be employed in a variety of lubricant basestocks comprising diverse oils of lubricating viscosity, including natural and synthetic lubricating oils and mixtures thereof.

Natural oils include animal oils, vegetable oils, mineral lubricating oils, solvent or acid treated mineral oils, and oils derived from coal or shale. Synthetic lubricating oils include hydrocarbon oils, halo-substituted hydrocarbon oils, alkylene oxide polymers, esters of carboxylic acids and polyols, esters of polycarboxylic acids and alcohols, esters of phosphorus-containing acids, polymeric tetrahydrofurans, silicon-based oils and mixtures thereof.

Specific examples of oils of lubricating viscosity are described in U.S. Pat. No. 4,326,972 and European Patent Publication 107,282, both herein incorporated by reference for their disclosures relating to lubricating oils. A basic, brief description of lubricant base oils appears in an article by D. V Brock, "Lubricant Base Oils", *Lubrication Engineering*, volume 43, pages 184–185, March, 1987. This article is herein incorporated by reference for its disclosures relating to lubricating oils. A description of oils of lubricating viscosity occurs in U.S. Pat. No. 4,582,618 (column 2, line 37 through column 3, line 63, inclusive), herein incorporated by reference for its disclosure to oils of lubricating viscosity.

The additives and components of this invention can be added directly to the lubricant. Preferably, however, they are diluted with a substantially inert, normally liquid organic diluent such as mineral oil, naphtha, toluene or xylene, to form an additive concentrate. These concentrates usually contain from about 10% to about 90% by weight of the components used in the composition of this invention and may contain, in addition, one or more other additives known in the art as described hereinabove. The remainder of the concentrate is the substantially inert normally liquid diluent.

The following Examples illustrate additive concentrates useful for preparing lubricating oil compositions. All percentages are by weight and are given on an oil or diluent free basis except for the products of the preceeding Examples in this specification which are not adjusted for diluent content.

| Components | Additive Concentrates (Weight %) | |
|---|---|---|
| | I | II |
| Polyisobutene (Mn(VPO) ~1700) substituted succinic anhydride/ ethylene polyamine reaction product | 27.47 | 25.57 |
| Oleylamide | 0.97 | 0.9 |
| Copper mixed secondary dialkyl dithiophosphate | 0.78 | 0.73 |
| Zinc mixed secondary dialkyl dithiophosphate | 8.95 | 9.16 |
| 2,4,6 - trialkyl phenol | 3.61 | 3.36 |
| Sodium overbased carboxylate | 5.97 | 5.56 |
| Product of Example 2 | 2.53 | |
| Product of Example 40 | | 9.09 |
| Silicone antifoam ppm (parts per million) | 780 ppm | 727 ppm |
| Mineral oil diluent | Balance to 100% | |

The following Examples illustrate several types of lubricants prepared employing the metal salts of this invention. These examples are for the purpose of illustration only and are not intended to be limiting in any way. Except for products of Examples provided herein, all amounts are on an oil-free basis.

EXAMPLES A-D

Gear Lubricants

Sun Oil Co. basestock+0.02% silicone antifoam+0.12% styrene-$C_{14-15}$ alkyl maleate copolymer further reacted with an amine+2.9% styrene-mixed $C_{8-18}$ alkyl maleate copolymer further reacted with an amine+components indicated in TABLE I below.

TABLE I

| Component | Lubricants (Weight %) | | | |
|---|---|---|---|---|
| | A | B | C | D |
| Product of Example 1 | 2.0 | 3.0 | | |
| Product of Example 2 | | | 2.0 | 3.0 |

EXAMPLES E-F

Marine Diesel Lubricants

Exxon SAE 40 basestock+0.3% polybutene substituted succinic anhydride+0.08% alkyl-phenoxy-ethoxyethanol+0.53% zinc salt of mixed primary alkyldithiophosphate+0.6% reaction product of polybutene succinic anhydride with ethylene polyamine+3.09% of mixed calcium overbased sulfurized tetrapropenyl phenol+0.18% carbonated calcium overbased alkylbenzene sulfonate+0.25% basic calcium alkylbenzene sulfonate+100 ppm silicone antifoam+0.02% polyoxyalkylene demulsifier+components indicated in TABLE II below.

TABLE II

| Component | Lubricants (Weight %) | |
|---|---|---|
| | E | F |
| Product of Example 14 | 5 | |
| Product of Example 3 | | 5 |

EXAMPLES G-K

Engine Oils

EXAMPLE G

An SAE 5W-30 engine oil is prepared containing Ashland/Valvoline basestock+0.017% of styrene-maleate copolymer reacted with an amine, 0.50% hydrogenated styrene-isoprene copolymer and 10.26% of the additive concentrate of Example I.

EXAMPLE H

An engine oil as described in Example G is prepared replacing 10.26% of the additive concentrate of Example I with 11.0% of the additive concentrate of Example II and adjusting the amount of basestock to total 100%.

EXAMPLES I-K

Engine oils having SAE 10W-30 viscosity are prepared containing Exxon basestocks, 0.016% styrene-maleate copolymer-amine post-treated, 0.67% hydrogenated styrene-butadiene copolymer, 2.57% polybutene (Mn (VPO)~1700) substituted succinic anhydride-ethylene polyamine reaction product, 0.1% oleylamide, 1.04% zinc mixed secondary alkyl dithiophosphate, 0.6% of sulfurized Dieis-Alder adduct of butadiene and butyl acrylate, 0.37% 2,4,6-trialkylphenol, 0.77% overbased sodium alkylbenzene sulfonate, 90 ppm of silicone antifoam and components indicated in TABLE III below.

TABLE III

| Components | Lubricants (Weight %) | | |
|---|---|---|---|
| | I | J | K |
| Product of Example 1 | 1 | | |
| Product of Example 40 | | 1 | |
| Product of Example 2 | | | 0.26 |

As indicated hereinabove, the metal salts of this invention may be used as additives for normally liquid fuels.

The fuels used in the fuel compositions of this invention are well known to those skilled in the art and usually contain a major portion of a normally liquid fuel such as hydrocarbonaceous petroleum distillate fuel (e.g., motor gasoline as defined by ASTM Specification D-439-73 and diesel fuel or fuel oil as defined in ASTM Specification D-396). Such fuels can also contain non-hydrocarbonaceous materials such as alcohols, ether, organo-nitro compounds and the like (e.g., methanol, ethanol, diethyl ether, methyl ethyl ether, nitromethane) are also within the scope of this invention as are liquid fuels derived from vegetable or mineral sources such as corn, alfalfa, shale and coal. Mixtures of fuels, such as mixtures of gasoline and alcohol, for example, methanol or ethanol are among the useful fuels.

Examples of fuel mixtures are combinations of gasoline and ethanol, diesel fuel and ether, gasoline and nitromethane, etc. Particularly preferred is gasoline, that is, a mixture of hydrocarbons having an ASTM boiling point of 60° C. at the 10% distillation point to about 205° C. at the 90% distillation point.

Generally, these fuel compositions contain an amount of at least one metal salt of this invention sufficient to impart anti-oxidant and/or dispersant and detergent properties to the fuel; usually this amount is about 1 to about 10,000, preferably 4 to 1,000, more preferably 10 to 500, parts by weight of the metal salt per million parts by weight of fuel. The preferred gasoline-based fuel compositions generally exhibit excellent dispersancy and detergency properties. In addition, they resist oxidation.

Fuel compositions may also contain other additives which are well known to those of skill in the art. These may include ethers, such as ethyl-t-butyl ether, methyl-t-butyl ether and the like, alcohols such as ethanol and methanol, lead scavengers such as halo-alkanes (e.g., ethylene dichloride and ethylene dibromide), dyes, cetane improvers, antioxidants such as 2,6 di-tertiary-butyl-4-methylphenol, rust inhibitors, such as alkylated succinic acids and anhydrides, bacteriostatic agents, gum inhibitors, metal deactivators, demulsifiers, upper cylinder lubricants, anti-icing agents and the like. The invention is useful with lead-free as well as lead-containing fuels.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A metal salt of the general formula $$A^{y-}M^{y+} \tag{I}$$

wherein M represents one or more metal ions, y is the total valence of all M and A represents one or more anion containing groups having a total of about y individual anionic moieties and each anion containing group is a group of the formula

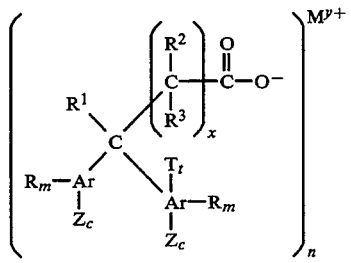

wherein T is selected from the group consisting of

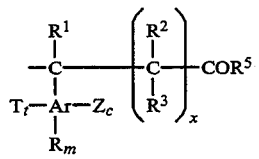

or

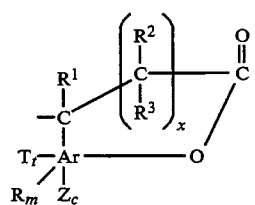

wherein each $R^5$ is independently selected from $O^-$ and $OR^6$ wherein $R^6$ is H or alkyl and t in Formula II is independently 0 or 1, when t in Formula II equals 1, from 1 up to about 3 additional groups T of formula V or VI are present, terminating when t in formula V or VI equals zero, wherein T is as hereinbefore defined and wherein each Ar is independently an aromatic group of from 4 to about 30 carbon atoms having from 0 to 3 optional substituents selected from the group consisting of polyalkoxyalkyl, lower alkoxy, nitro, halo or combinations of two or more of said optional substituents, each R is independently alkyl, alkenyl or aryl containing at least 8 carbon atoms, $R^1$ is H or a hydrocarbyl group, $R^2$ and $R^3$ are each independently H or a hydrocarbyl group, each m is independently an integer ranging from 1 to about 10, x ranges from 0 to about 8, and each Z is independently OH, $(OR^4)_bOH$ or $O^-$ wherein each $R^4$ is independently a divalent hydrocarbyl group and b is a number ranging from 1 to about 30 and c ranges from 0 to about 3 with the proviso that when t in Formula (II)=0, or when T is Formula (V), then c is not 0, provided that the sum of m, c and t does not exceed the valences of the corresponding Ar.

2. A metal salt according to claim 1 wherein t in Formula (II) is 0.

3. A metal salt according to claim 1 wherein t in Formula (II) is 1.

4. A metal salt according to claim 3 wherein T is a group having the structure given by Formula (V).

5. A metal salt according to claim 3 wherein T is a group having the structure given by Formula (VI).

6. A metal salt according to claim 1 having at least one R containing from 8 to about 600 carbon atoms.

7. A metal salt according to claim 6 wherein each R is independently an aliphatic group.

8. A metal salt according to claim 1 wherein m equals 1 and R is an alkyl or alkenyl group.

9. A metal salt according to claim 8 wherein R contains from 30 to about 100 carbon atoms and is derived from homopolymerized and interpolymerized $C_{2-10}$ olefins, 10. A metal salt according to claim 9 wherein the olefins are 1-olefins.

11. A metal salt according to claim 10 wherein the 1-olefins are ethylene, propylene, butenes and mixtures thereof.

12. A metal salt according to claim 8 wherein R contains from 8 to about 24 carbon atoms.

13. A metal salt according to claim 8 wherein R contains from 12 to about 50 carbon atoms.

14. A metal salt according to claim 1 wherein each Ar is independently a single ring aromatic group, a fused ring aromatic group or a linked aromatic group.

15. A metal salt according to claim 14 wherein at least one Ar is a linked aromatic group corresponding to the formula

wherein each ar is a single ring or a fused ring aromatic nucleus of 4 to about 12 carbons, w is an integer ranging from 1 to about 20 and each L is independently selected from the group consisting of carbon to carbon single bonds between ar nuclei, ether linkages, sulfide linkages, polysulfide linkages, sulfinyl linkages, sulfonyl linkages, lower alkylene linkages, lower alkylene ether linkages, lower alkylene sulfide and/or polysulfide linkages, amino linkages derived from oxo- or keto- carboxylic acids of the formula

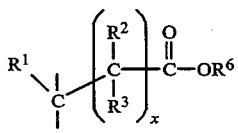

wherein each of $R^1$ $R^2$ and $R^3$ is independently alkyl or alkenyl or H, $R^6$ is H or an alkyl group and x is an integer ranging from 0 to about 8, and mixtures of such linkages.

16. A metal salt according to claim 13 wherein at least one Ar is a member of the group consisting of a benzene nucleus, a lower alkylene bridged benzene nucleus or a naphthalene nucleus.

17. A metal salt according to claim 1 wherein each of $R^1$ $R^2$ and $R^3$ is independently hydrogen or a lower alkyl or alkenyl group.

18. A metal salt according to claim 1 wherein at least one Z is —OH.

19. A metal salt according to claim 18 wherein each c is 1 and one Z is $O^-$.

20. A metal salt according to claim 1 wherein M is an alkali or alkaline earth metal.

21. A metal salt according to claim 20 wherein M is sodium or lithium.

22. A metal salt according to claim 1 wherein at least one Z is $(OR^4)_bOH$.

23. A metal salt according to claim 22 wherein $R^4$ is a lower alkylene group.

24. A metal salt according to claim 16 wherein each Z is OH, m and c are each one, x is 0, and Ar has no optional substituents, and $R^1=H$.

25. A metal salt of the formula

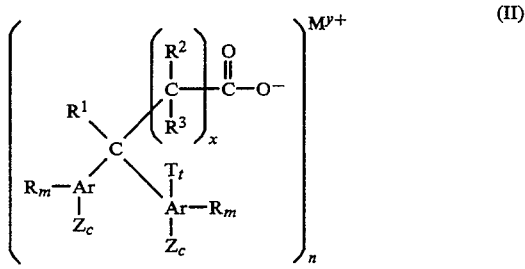
(II)

wherein M represents one or more metal ions, y is the total valence of all M, n is a number depending on the value of y, n times the number of anionic moieties in the corresponding parenthetical group is about equal to y, each Ar is independently a benzene nucleus, a lower alkylene bridged benzene nucleus or a naphthalene nucleus, wherein T is selected from the group consisting of

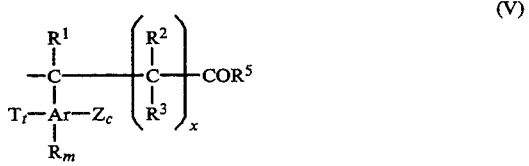
(V)

or

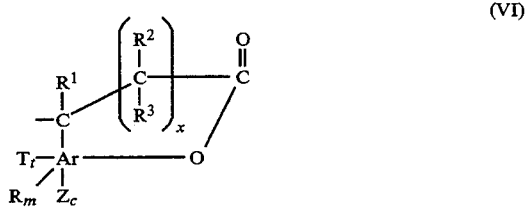
(VI)

wherein each $R^5$ is independently selected from $O^-$ and $OR^6$ wherein $R^6$ is H or alkyl and t in Formula II is independently 0 or 1, when t in Formula II equals 1, from 1 up to about 3 additional groups T of Formula V or VI are present, terminating when t in Formula V or VI equals zero, each Ar has 0 or 1 optional substituents selected from the group consisting of lower alkyl, lower alkoxy, polyalkoxyalkyl, nitro or halo, T is as hereinbefore defined, each R is independently an aliphatic hydrocarbyl group wherein at least one R has at least 8 carbon atoms, $R^1$ is H or an aliphatic group, $R^2$ and $R^3$ are each independently H or an aliphatic group, each m is independently an integer ranging from 1 to about 3, x ranges from 0 to about 8, and each Z is independently OH, $(OR^4)_bOH$ or $O^-$ wherein each $R^4$ is independently a divalent hydrocarbyl group and b is a number ranging from 1 to about 30 and c ranges from 0 to about 2 with the proviso that when t in Formula (II)=0, or when T is Formula (V), then c is not 0 provided that the sum of m, c and t does not exceed the unsatisfied valences of the corresponding Ar.

26. A metal salt according to claim 25 wherein t in Formula (II) is 0.

27. A metal salt according to claim 25 wherein t in Formula (II) is 1.

28. A metal salt according to claim 27 wherein T is a group having the structure given by Formula (V).

29. A metal salt according to claim 27 wherein T is a group having the structure given by Formula (VI).

30. A metal salt according to claim 25 wherein at least one R contains from 12 to about 100 carbon atoms and m is 1 or 2.

31. A metal salt according to claim 30 wherein R is a substantially saturated aliphatic group.

32. A metal salt, according to claim 25 wherein $R^1$ is H or a lower alkyl group, $R^2$ and $R^3$ are independently H or a lower alkyl group and x is 0, 1 or 2.

33. A metal salt according to claim 30 wherein R contains from about 8 to about 24 carbon atoms and each m is 1.

34. A metal salt according to claim 30 wherein R contains at least about 30 carbon atoms and m is 1.

35. A metal salt according to claim 30 wherein R contains from 12 to about 50 carbon atoms and m is 1.

36. A metal salt according to claim 25 wherein Ar is a benzene nucleus and Z is OH.

37. A metal salt according to claim 36 wherein c is 1.

38. A metal salt according to claim 25 wherein M is a metal ion selected from the group consisting of alkali metals, alkaline earth metals, copper, manganese, iron, zinc and nickel.

39. A metal salt according to claim 38 wherein M is sodium or lithium.

40. A metal salt of the formula

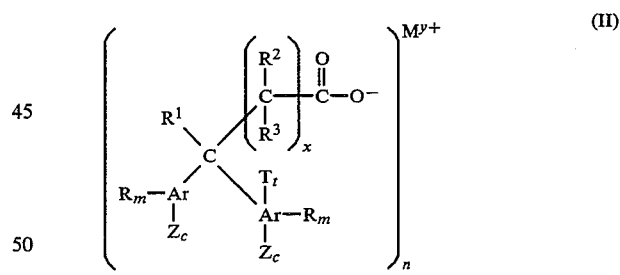
(II)

wherein M represents one or more metal ions, y is the valence of all M, and n is a number depending on the value of y, n times the number of anionic moieties in the corresponding parenthetical group is about equal to y, wherein T is selected from the group consisting of

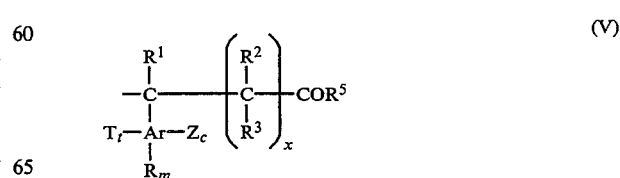
(V)

or

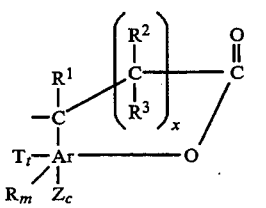

wherein each $R^5$ is independently selected from $O^-$ and $OR^6$ wherein $R^6$ is H or alkyl and t in Formula II is independently 0 or 1, when t in Formula II equals 1, from 1 up to about 3 additional groups T of Formula V or VI are present, terminating when t in Formula V or VI equals zero, wherein each Ar is independently an aromatic group of from 4 to about 30 carbon atoms having from 0 to 3 optional substituents selected from the group consisting of polyalkoxyalkyl, lower alkoxy, nitro, halo or combinations of two or more of said optional substituents, wherein T is as hereinbefore defined, each R is independently alkyl or alkenyl containing at least about 8 carbon atoms, at least one Ar is an aromatic group of the formula

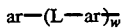

wherein each ar is a single ring or a fused ring aromatic nucleus of 4 to 12 carbons, w is an integer ranging from 1 to about 20 and each L is independently selected from the group consisting of carbon to carbon single bonds between ar nuclei, ether linkages, sulfide linkages, polysulfide linkages, sulfinyl linkages, sulfonyl linkages, lower alkylene linkages, lower alkylene ether linkages, lower alkylene sulfide and/or polysulfide linkages, amino linkages, linkages derived from oxo- or ketocarboxylic acids of the formula

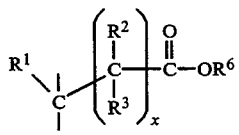

wherein each of $R^1$ $R^2$ and $R^3$ is independently lower alkyl or H, $R^6$ is H or an alkyl group and x is an integer ranging from 0 to about 8, and mixtures of such linkages, at least one ar has a substituent R wherein each R is independently alkyl or alkenyl containing at least 8 carbon atoms, each Z is OH, $(OR^4)_bOH$ or $O^-$, $R^4$ is an alkylene group, and b ranges from 1 to about 10, each of $R^1$, $R^2$ and $R^3$ is independently H or lower alkyl, x ranges from 0 to 3, m ranges from 1 up to about 10 and c is a number ranging from 0 to about 3 provided that when t in Formula (II)=0, or when T is Formula (V), then c is not zero provided that the sum of m, c and t does not exceed the unsatisfied valences of the corresponding Ar.

41. A metal salt according to claim 40 wherein t in Formula (II) is 0.

42. A metal salt according to claim 40 wherein t in Formula (II) is 1.

43. A metal salt according to claim 42 wherein T is a group having the structure given by Formula (V).

44. A metal salt according to claim 42 wherein T is a group having the structure given by Formula (VI).

45. A metal salt according to claim 40 wherein L is selected from the group consisting of ether linkages, sulfide and/or polysulfide linkages, lower alkylene linkages or carbon to carbon single bonds between ar nuclei.

46. A metal salt according to claim 40 wherein at least one ar is a benzene nucleus or a naphthalene nucleus and w is 1, 2 or 3.

47. A metal salt according to claim 40 wherein M is a metal ion and Z is selected from OH and $O^-$.

48. A metal salt according to claim 47 wherein at least one Z is OH and at least one Z is $O^-$.

49. A metal salt according to claim 47 wherein the metal is lithium or sodium.

50. A metal salt according to claim 40 wherein each ar has one substituent R having from 4 to about 100 carbon atoms and there are substantially no optional substituents on ar.

51. A metal salt of the formula

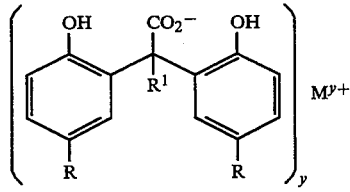

wherein M represents one or more metal ions, y is the total valence of all M, $R^1$ is H or an alkyl or alkenyl group containing from 1 to about 20 carbon atoms and each R is independently a hydrocarbyl group containing from 12 to about 300 carbon atoms.

52. A metal salt according to claim 51 wherein each R independently contains from 12 to about 24 carbon atoms.

53. A metal salt according to claim 51 wherein each R independently contains an average of at least 30 carbon atoms.

54. A metal salt according to claim 51 wherein each R is derived from polymerized or interpolymerized $C_{2-10}$ olefins.

55. A metal salt according to claim 54 wherein the olefin is propylene and R has a number average molecular weight ranging from 300 to about 800.

56. A metal salt according to claim 51 wherein each R contains from 12 to about 50 carbon atoms.

57. A metal salt according to claim 51 wherein M is an alkali metal, an alkaline earth metal copper, manganese, iron, zinc or nickel.

58. A metal salt according to claim 57 wherein M is lithium or sodium.

59. A process which comprises reacting at an elevated temperature
(a) a compound of the formula

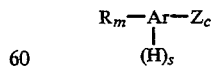

wherein R is alkyl or alkenyl having from 8 to about 100 carbon atoms, m is a number ranging from 1 to about 3, Ar is an aromatic group containing from 4 to about 30 carbon atoms having from 0 to 3 optional substituents selected from the group consisting of lower alkyl, lower alkoxy, nitro, halo, or combinations of 2 or more said optional substituents, s is an integer of at least 1 and wherein the total of s +m does not exceed the available valences of Ar, and Z is selected from the group consisting of OH or $(OR^4)_bOH$ wherein each $R^4$ is independently a divalent hydrocarbyl group and b is a number ranging from 1 to about 30 and c ranges from 1 to about 3, with (b) a carboxylic compound of the formula $$R^1CO(CR^2R^3)_xCOOH$$

wherein $R^1$, $R^2$ and $R^3$ are independently H or a hydrocarbyl group, and X is an integer ranging from 0 to about 8 and then reacting the intermediate so formed with a metal-containing reactant to form a salt.

60. A process according to claim 59 wherein said at least one R contains from 8 to about 24 carbon atoms.

61. A process according to claim 59 wherein at least one R contains at least 30 carbon atoms.

62. A process according to claim 59 wherein Z is OH.

63. A process according to claim 59 wherein Ar is selected from the group consisting of a benzene nucleus, a lower alkylene coupled benzene nucleus or a napthalene nucleus.

64. A process according to claim 59 wherein each of $R^1$ $R^2$ and $R^3$ is H and x equals 0 or 1.

65. A process according to claim 59 wherein the metal-containing reactant is an alkali or alkaline earth metal-containing compound.

66. A process according to claim 59 wherein the process is conducted in the presence of a catalyst.

67. A process according to claim 66 wherein the catalyst is an acidic compound.

68. A composition prepared by the process of claim 59.

69. A fuel composition comprising a major proportion of normally liquid fuel and about 1–10,000 parts by weight, per million parts of the fuel composition, of at least one metal salt as claimed in claim 1.

70. A fuel composition comprising a major proportion of normally liquid fuel and about 1–10,000 parts by weight, per million parts of the fuel composition, of at least one compound as claimed in claim 25.

71. A fuel composition comprising a major proportion of normally liquid fuel and about 1–10,000 parts by weight, per million parts of the fuel composition, of at least one compound as claimed in claim 68.

72. A lubricating oil composition other than a 2-cycle engine oil comprising a major proportion of at least one oil of lubricating viscosity and a minor amount of at least one compound as claimed in claim 1.

73. A lubricating oil composition other than a 2-cycle engine oil comprising a major proportion of at least one oil of lubricating viscosity and a minor amount of at least one compound as claimed in claim 25.

74. A lubricating oil composition other than a 2-cycle engine oil comprising a major proportion of at least one oil of lubricating viscosity and a minor amount of at least one compound as claimed in claim 68.

75. An additive concentrate for preparing lubricant or fuel compositions other than 2-cycle engine lubricants or fuel compositions comprising from about 10 to about 90 percent by weight of a substantially inert diluent and from about 10 to about 90% by weight of at least one compound of the general formula $$A^{y-}M^{y+} \qquad (I)$$

wherein M represents one or more metal ions, y is the total valence of all M and A represents one or more anion containing groups having a total of about y individual anionic moieties and each anion containing group is a group of the formula

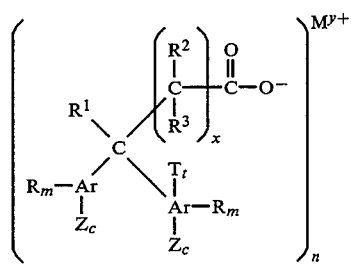

wherein T is selected from the group consisting of

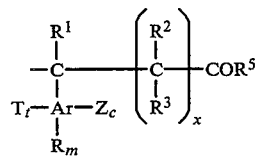

or

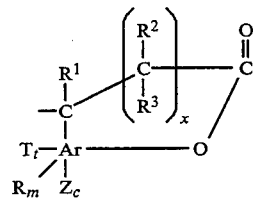

wherein each $R^5$ is independently selected from $O^-$ and $OR^6$ wherein $R^6$ is H or alkyl and t in Formula II is independently 0 or 1, when t in Formula II equals 1, from 1 up to about 3 additional groups T of Formula V or VI are present, terminating when t in Formula, V or VI equals zero, wherein each Ar is independently an aromatic group of from 4 to about 30 carbon atoms having from 0 to 3 optional substituents selected from the group consisting of polyalkoxyalkyl, lower alkoxy, nitro, halo or combinations of two or more of said optional substituents, wherein each T is as hereinbefore defined, each R is independently alkyl, alkenyl or aryl containing at least 8 carbon atoms, $R^1$ is H or a hydrocarbyl group, $R^2$ and $R^3$ are each independently H or a hydrocarbyl group, each m is independently 0 or an integer ranging from 1 to about 10, x ranges from 0 to about 8, and each Z is independently OH, $(OR^4)_bOH$ or $O^-$ wherein each $R^4$ is independently a divalent hydrocarbyl group and b is a number ranging from 1 to about 30 and c ranges from 0 to about 3 with the proviso that when t in Formula (II)=0, or when T is Formula V, then c is not 0 provided that the sum of m, c and t does not exceed the unsatisfied valences of the corresponding Ar.

* * * * *